(12) United States Patent
Uemura et al.

(10) Patent No.: US 8,262,581 B2
(45) Date of Patent: Sep. 11, 2012

(54) SOLID TISSUE IMPEDANCE ESTIMATING METHOD, CARDIAC OUTPUT CALCULATING METHOD, PULMONARY ARTERY WEDGE PRESSURE CALCULATING METHOD, CARDIAC OUTPUT MONITORING DEVICE, CARDIAC OUTPUT MONITORING SYSTEM, PULMONARY ARTERY WEDGE PRESSURE MONITORING DEVICE, AND PULMONARY ARTERY WEDGE PRESSURE MONITORING SYSTEM

(75) Inventors: Kazunori Uemura, Osaka (JP); Masashi Inagaki, Chiba (JP); Masaru Sugimachi, Osaka (JP); Kazuo Shimizu, Tokyo (JP); Masatoshi Kobayashi, Tokyo (JP)

(73) Assignees: National Cerebral and Cardiovascular Center, Osaka (JP); Olympus Corporation, Tokyo (JP)

( * ) Notice: Subject to any disclaimer, the term of this patent is extended or adjusted under 35 U.S.C. 154(b) by 1307 days.

(21) Appl. No.: 11/950,169

(22) Filed: Dec. 4, 2007

(65) Prior Publication Data

US 2008/0139958 A1 Jun. 12, 2008

(30) Foreign Application Priority Data

Dec. 11, 2006 (JP) .................................. 2006-333691

(51) Int. Cl.
*A61B 5/02* (2006.01)

(52) U.S. Cl. ........................................ 600/526; 600/508
(58) Field of Classification Search .................. 600/481, 600/508, 526
See application file for complete search history.

(56) References Cited

U.S. PATENT DOCUMENTS

| | | | |
|---|---|---|---|
| 4,450,527 A | 5/1984 | Sramek | |
| 4,674,518 A | 6/1987 | Salo | |
| 5,058,583 A | 10/1991 | Geddes et al. | |
| 5,417,717 A | 5/1995 | Salo et al. | |
| 6,438,408 B1 | 8/2002 | Mulligan et al. | |
| 6,473,640 B1 | 10/2002 | Erlebacher | |
| 6,595,927 B2 | 7/2003 | Pitts-Crick et al. | |
| 6,829,503 B2 | 12/2004 | Alt | |
| 2005/0137636 A1* | 6/2005 | Gunderson et al. | 607/27 |

* cited by examiner

*Primary Examiner* — Tammie K Heller
(74) *Attorney, Agent, or Firm* — Scully, Scott, Murphy & Presser, P.C.

(57) ABSTRACT

A practical method for estimating cardiac output and pulmonary artery wedge pressure with good accuracy is provided. A method is provided for estimating the impedance arising from solid tissue by determining the impedance at the intersection between the line of identity and the extrapolated regression line, where the regression line is obtained by linearly regressing the maximum value to the minimum value of the impedance signal of each of multiple data sets, where each data set contains the maximum value and the minimum value of the impedance signal during one cardiac cycle, where impedance signal is obtained between a can electrode implanted in the left thoracic wall and an electrode inserted into the coronary vein, over a specific period of time following the infusion of hypertonic saline into the pulmonary circulation.

3 Claims, 6 Drawing Sheets

SOLID TISSUE IMPEDANCE ESTIMATING METHOD, CARDIAC OUTPUT CALCULATING METHOD, PULMONARY ARTERY WEDGE PRESSURE CALCULATING METHOD, CARDIAC OUTPUT MONITORING DEVICE, CARDIAC OUTPUT MONITORING SYSTEM, PULMONARY ARTERY WEDGE PRESSURE MONITORING DEVICE, AND PULMONARY ARTERY WEDGE PRESSURE MONITORING SYSTEM

CROSS-REFERENCE TO RELATED APPLICATIONS

This application claims benefit of Japanese Application No. 2006-333691, filed in Japan on Dec. 11, 2006.

BACKGROUND OF THE INVENTION

1. Field of the Invention

The present invention relates to a solid tissue impedance estimating method, a cardiac output calculating method, a pulmonary artery wedge pressure calculating method, a cardiac output monitoring device, a cardiac output monitoring system, a pulmonary artery wedge pressure monitoring device and a pulmonary artery wedge pressure monitoring system.

This application is based on Japanese Patent Application No. 2006-333691, the content of which is incorporated herein by reference.

2. Description of Related Art

If changes in cardiac function can be continuously monitored in patients with heart failure who are implanted with devices such as implantable defibrillator or cardiac resynchronization device, it becomes possible to (1) adjust therapy in response to each patient's condition, and (2) detect cardiac deterioration earlier and initiate therapy sooner. As a result, patient prognosis or quality of life (QOL) indicators such as duration of hospital stay, etc. can be improved. For this reason, cardiac function monitors that can be incorporated into implantable devices are necessary from a clinical viewpoint.

Measuring and evaluating both cardiac output and pulmonary artery wedge pressure are generally known as necessary techniques for evaluating cardiac function. Examples of conventional techniques for measuring or estimating cardiac output include those disclosed in the Publications of U.S. Pat. No. 4,450,527, U.S. Pat. No. 5,417,717, U.S. Pat. No. 5,058,583 and U.S. Pat. No. 6,438,408. Examples of conventional techniques for estimating pulmonary artery wedge pressure or the degree of pulmonary congestion include those disclosed in the Publications of U.S. Pat. No. 6,473,640, U.S. Pat. No. 6,595,927, and U.S. Pat. No. 6,829,503.

The method disclosed in the Publication of U.S. Pat. No. 4,450,527 measures the impedance between electrodes placed on the body surface. As a result, electrode position and electrode impedance can vary due to body movement or perspiration, so that an accurate estimate of cardiac output is not possible. Moreover, since it is not realistic to attach electrodes on the body surface for an extended period of time, this method is not suitable for long-term monitoring.

The methods disclosed in the Publications of U.S. Pat. No. 5,417,717 and U.S. Pat. No. 5,058,583 estimate cardiac output from changes in right ventricular volume using an electrode placed within the right ventricle. However, the accuracy of these estimates has not been proven. The method in the Publication U.S. Pat. No. 6,438,408 estimates cardiac output from changes in left ventricular volume using an electrode inserted within the left ventricle. However, since the electrode remains within the patient's left ventricle for a long time, problems such as thrombosis and infection occur. Accordingly, it is difficult to put this method to practical use.

The methods disclosed in the Publications of U.S. Pat. No. 6,473,640 and U.S. Pat. No. 6,595,927 measure the time-averaged impedance between a can electrode implanted in the thoracic wall and a lead in the right ventricle or the right atrium, to estimate the degree of pulmonary congestion. Accordingly, changes in the right ventricular or right atrial volume are partially included in the signals. As a result, if there is a dilatation of the right ventricular volume, this can be misinterpreted as pulmonary congestion, even when no pulmonary congestion is present, i.e., even when there is no abnormality in the pulmonary artery wedge pressure.

The method disclosed in the Publication of U.S. Pat. No. 6,829,503 estimates the degree of pulmonary congestion by measuring the time-averaged impedance of the lungs, using a can electrode embedded in the thoracic wall. In this method, the pulmonary circulatory blood volume is estimated from the time-averaged pulmonary impedance signal, and the degree of pulmonary congestion is estimated. However, theoretically, pulmonary artery wedge pressure or the degree of pulmonary congestion is determined not only by the pulmonary circulatory blood volume but also by the cardiac output. For example, it is known that the pulmonary artery wedge pressure increases when the cardiac output becomes lower, even if the pulmonary circulatory blood volume is the same. The method disclosed in the Publication of U.S. Pat. No. 6,829,503 does not take changes in cardiac output into account, so that the estimate of the degree of pulmonary congestion is not accurate.

Further, in each of the cases of the Publications of U.S. Pat. No. 6,473,640, U.S. Pat. No. 6,595,927, and U.S. Pat. No. 6,829,503, it is not possible to estimate the values of pulmonary artery wedge pressure.

BRIEF SUMMARY OF THE INVENTION

The present invention is produced considering the above-described circumstances, and its objective is to provide a realistic solid tissue impedance estimating method which can be practically applied to estimate cardiac output with good accuracy, a cardiac output calculating method, a pulmonary artery wedge pressure calculating method, a cardiac output monitoring device, a cardiac output monitoring system, a pulmonary artery wedge pressure monitoring device and a pulmonary artery wedge pressure monitoring system.

The present invention provides the following means to achieve the above objective.

The first embodiment of the present invention is a method for estimating the impedance arising from solid tissue by determining the impedance at the intersection between the line of identity and the extrapolated regression line, where the regression line is obtained by linearly regressing the maximum value to the minimum value of the impedance signal of each of multiple data sets, where each data set contains the maximum value and the minimum value of the impedance signal during one cardiac cycle, where impedance signal is obtained between a can electrode implanted in the left thoracic wall and an electrode inserted into the coronary vein, over a specific period of time following the infusion of hypertonic saline into the pulmonary circulation.

The impedance between the can electrode implanted in the left thoracic wall and the electrode inserted into the coronary vein is expressed as the sum of the impedance arising from solid tissues other than blood such as pleura, pericardium or the musculature of the thoracic wall, and the impedance arising from the pulmonary circulatory blood, both of which are within the effective conductive volume.

The electrical impedance of the pulmonary circulatory blood volume falls during the specific period of time following infusion of the hypertonic saline into the pulmonary circulation. Accordingly, there is a decline in the detected impedance signal.

By plotting the maximum value against minimum value of the impedance signal of each of multiple data sets, a linear regression line can be calculated. By obtaining the impedance signal at the intersection of the line of identity and the regression line, where the maximum and the minimum value of the impedance signal is the same, and this corresponds to the impedance at the putative state of no pulsation, one can estimate accurately the solid tissue impedance that is independent of the pulmonary circulatory blood volume.

The second embodiment of the present invention is a cardiac output and pulmonary artery wedge pressure calculating method in which the cardiac output and the pulmonary artery wedge pressure are calculated by the following formulae based on the solid tissue impedance estimated by the preceding estimating method and the maximum, minimum and mean values of the measured impedance signal during one unperturbed cardiac cycle:

$$CO = k \times (1/(Zmin - Zs) - 1/(Zmax - Zs)) \times HR \quad (A)$$

where CO: cardiac output; k: correction factor; Zmin: minimum impedance signal; Zmax: maximum impedance signal; Zs: solid tissue impedance; and HR: heart rate:

$$PAWP = A \times C/(Zmean - Zs) - CO \times B \quad (B)$$

where PAWP: pulmonary artery wedge pressure; A, B, C: correction factors, and Zmean: mean impedance signal.

In the second embodiment of the present invention, cardiac output and the pulmonary artery wedge pressure can be calculated with good accuracy using an accurate estimate of solid tissue impedance. By accurately calculating the cardiac output and the pulmonary artery wedge pressure, changes in cardiac function can be continuously monitored. As a result, therapy can be adjusted in response to each patient's condition, and treatment can be initiated sooner by earlier detection of undesirable changes. Accordingly, it is possible to achieve an improvement in better patient prognosis and QOL indicators such as shorter hospital stays, etc.

Moreover, it is possible to rapidly diagnose cardiac arrhythmias from changes in cardiac output and pulmonary artery wedge pressure in a short time interval, enabling more appropriate operations of the implantable defibrillator where various means of the present invention are incorporated.

The third embodiment of the present invention is a cardiac output monitoring device and a pulmonary artery wedge pressure monitoring device that includes a regression line calculating means which inputs multiple data sets containing the maximum value and the minimum value during each of multiple cardiac cycles of the impedance signal between a can electrode implanted in the left thoracic wall and an electrode inserted into the coronary vein, the data sets being obtained over a specific period of time following the infusion of hypertonic saline into the pulmonary circulation, and calculates the regression line between the maximum value and the minimum value of the impedance signal; and a solid tissue impedance estimating means that estimates the solid tissue impedance by determining the impedance at the intersection between the line of identity and the extrapolated regression line.

In the third embodiment of the invention, the regression line between the maximum value and the minimum value of the impedance signal during multiple cardiac cycles is calculated by a regression line calculating means, and the solid tissue impedance is estimated by determining the impedance at the intersection between the line of identity and the extrapolated regression line by a solid tissue impedance estimating means. Cardiac output and pulmonary artery wedge pressure can then be continuously monitored with high accuracy by using this accurate estimate of the solid tissue impedance.

The third embodiment of the present invention may include a cardiac output calculating means and a pulmonary artery wedge pressure calculating means for calculating cardiac output and pulmonary artery wedge pressure using the following formulae and the solid tissue impedance estimated by the solid tissue impedance estimating means, and the maximum, minimum and mean values of the measured impedance signal during one unperturbed cardiac cycle:

$$CO = k \times (1/(Zmin - Zs) - 1/(Zmax - Zs)) \times HR \quad (A)$$

where CO: cardiac output; k: correction factor; Zmin: minimum impedance signal; Zmax: maximum impedance signal; Zs: solid tissue impedance; and HR: heart rate, $$PAWP = A \times C/(Zmean - Zs) - CO \times B \quad (B)$$

where PAWP: pulmonary artery wedge pressure; A, B, C: correction factors, and Zmean: mean impedance signal.

By providing this embodiment, one can calculate cardiac output and pulmonary artery wedge pressure accurately using an accurate estimate of solid tissue impedance. By accurately calculating cardiac output and pulmonary artery wedge pressure, it is possible to continuously monitor trends in cardiac function. Thus, therapy can be adjusted in response to each patient's condition, and treatment can be initiated sooner by earlier detection of undesirable changes. Accordingly, it is possible to achieve an improvement in better patient prognosis and QOL indicators such as shorter hospital stays, etc.

Moreover, it is possible to rapidly diagnose cardiac arrhythmias from changes in cardiac output and pulmonary artery wedge pressure in a short time interval, enabling more appropriate operations of the implantable defibrillator where various means of the present invention are incorporated.

The fourth embodiment of the present invention is a cardiac output and pulmonary artery wedge pressure monitoring system that includes an electrode inserted in the coronary vein; a can electrode implanted in the left thoracic wall; an impedance signal detecting means which injects a constant current between these electrodes, and detects the impedance signal between these electrodes or between another electrode in the coronary vein and the can electrode; and a cardiac output and pulmonary artery wedge pressure monitoring device that inputs the impedance signal detected by the impedance signal detecting means.

The use of the electrode inserted into the coronary vein and the can electrode implanted in the left thoracic wall can be shared for the operation of an implantable defibrillator or a cardiac resynchronization device, and for continuous accurate monitoring of cardiac output and pulmonary artery wedge pressure.

The present invention enables a practical accurate method for estimating cardiac output and pulmonary artery wedge pressure and a device for these estimations.

DETAILED DESCRIPTION OF THE INVENTION

The cardiac output and pulmonary artery wedge pressure monitoring system 1 according to an embodiment of the present invention will be explained with reference to FIGS. 1 to 7.

Figure 1:
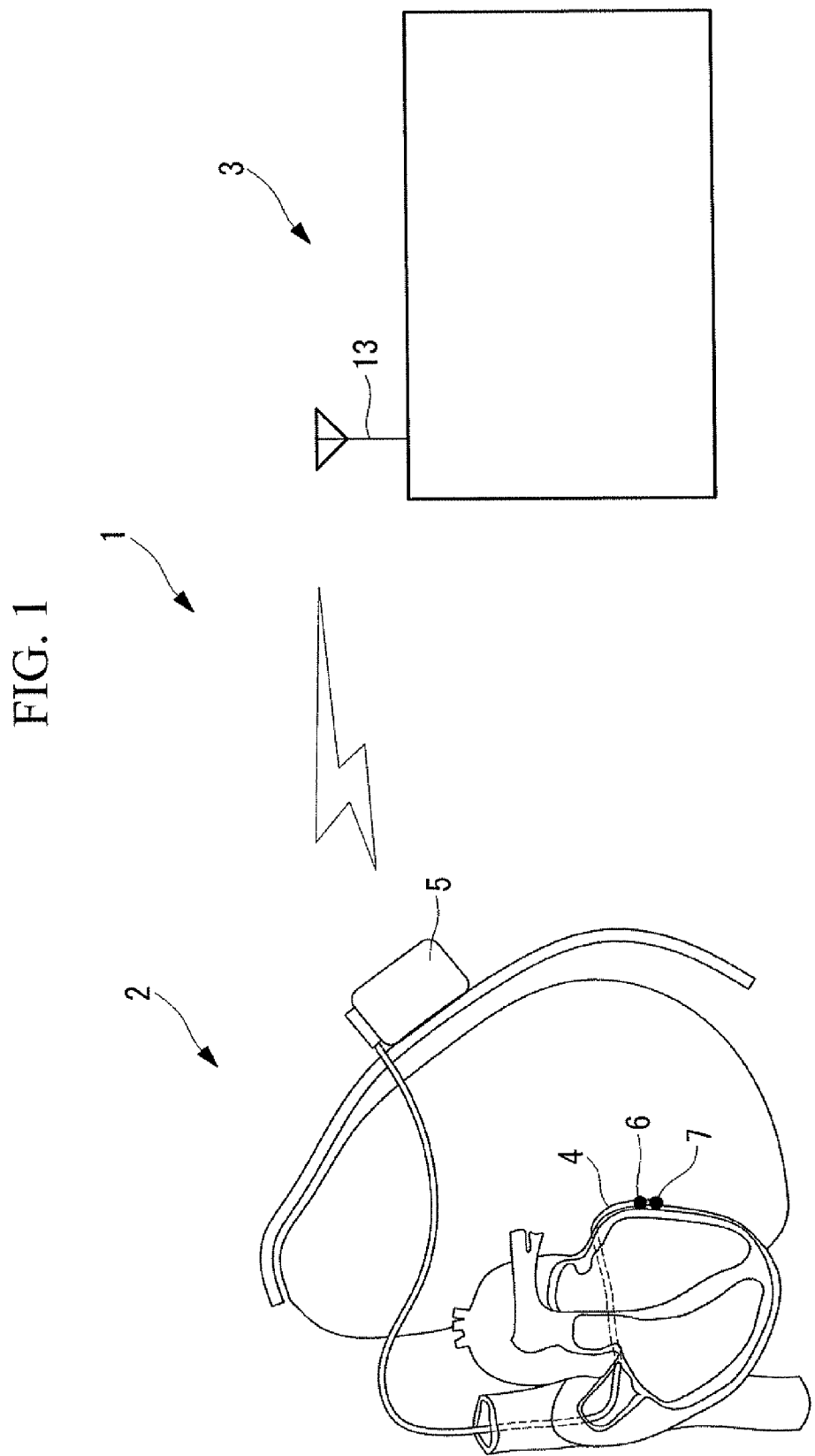
FIG. 1 is a comprehensive structural diagram showing the cardiac output and pulmonary artery wedge pressure monitoring system according to an embodiment of the present invention.

As shown in FIG. 1, the cardiac output and pulmonary artery wedge pressure monitoring system 1 according to this embodiment includes an implantable defibrillator (serving as an impedance signal detecting means) 2 that is implanted in a patient with heart failure; and a cardiac output and pulmonary artery wedge pressure monitoring device 3 that is placed outside of the body of the patient and estimates cardiac output and pulmonary artery wedge pressure based on the impedance signal detected by the implantable defibrillator 2.

Figure 2:
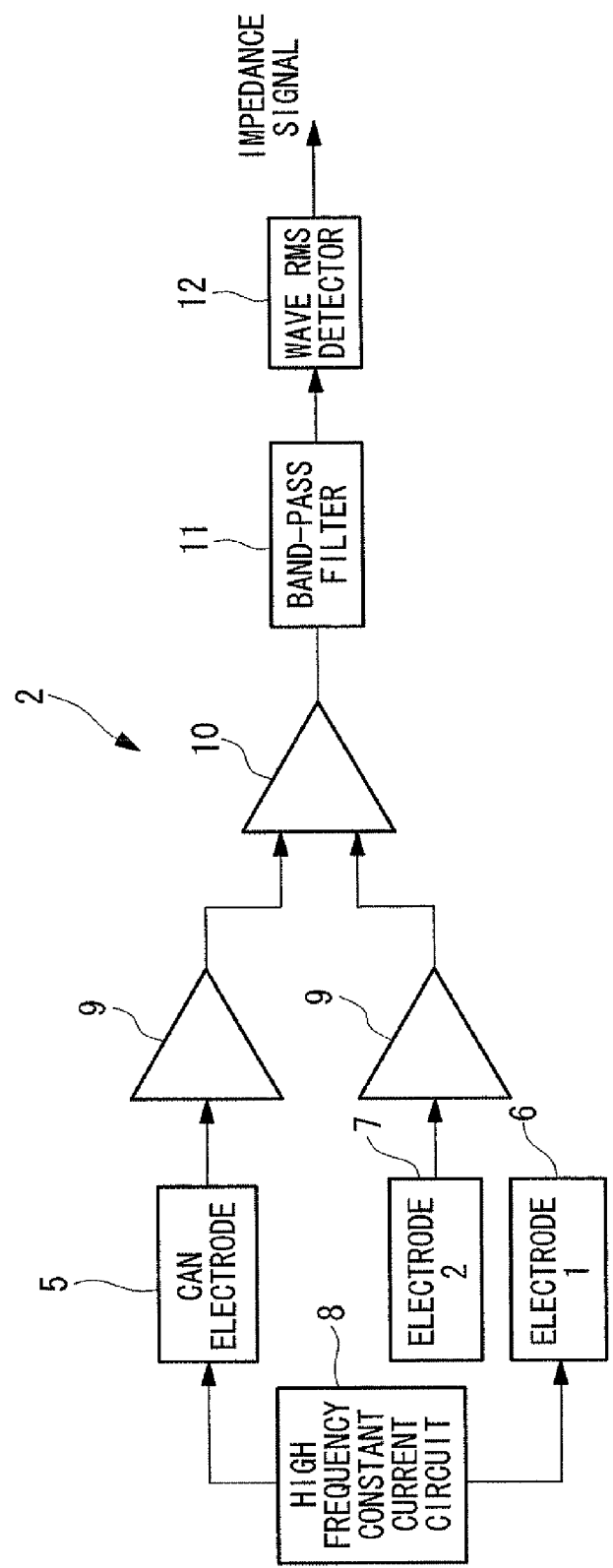
FIG. 2 is a block diagram showing the circuit structure of the cardiac output and pulmonary artery wedge pressure monitoring system shown in FIG. 1 and is incorporated in e.g., implantable defibrillators.

The implantable defibrillator 2 is equipped with a coronary vein electrode-tipped catheter 4 that is inserted into the coronary vein; and a can electrode 5 (i.e., the chassis of the defibrillator itself) that is implanted in the left thoracic wall. The coronary vein catheter 4 has two electrodes 6, 7. As shown in FIG. 2, a current generator 8 is connected between the can electrode 5 and the first electrode 6 to provide a constant-amplitude alternating current with frequency of 2 to 20 kHz between the electrodes 5, 6.

As shown in FIG. 2, an amplifying circuit (amplifier 9 and differential amplifier 10) is connected to the can electrode 5 and the second electrode 7. A band-pass filter 11 and a wave root-mean-square (RMS) detector 12 are connected to the amplifying circuit 9, 10.

The voltage signal generated between the second electrode 7 and the can electrode 5 is amplified by the amplifying circuit 9, 10. After frequency components other than that of the exciting alternating current have been removed by the band-pass filter 11, the RMS voltage of the frequency component of the exciting alternating current is obtained by the wave RMS detector 12.

The RMS voltage signal obtained above linearly correlates with the impedance. The impedance signal can be obtained by calibrating the RMS voltage signal against the resistors with known resistance value.

Figure 3:
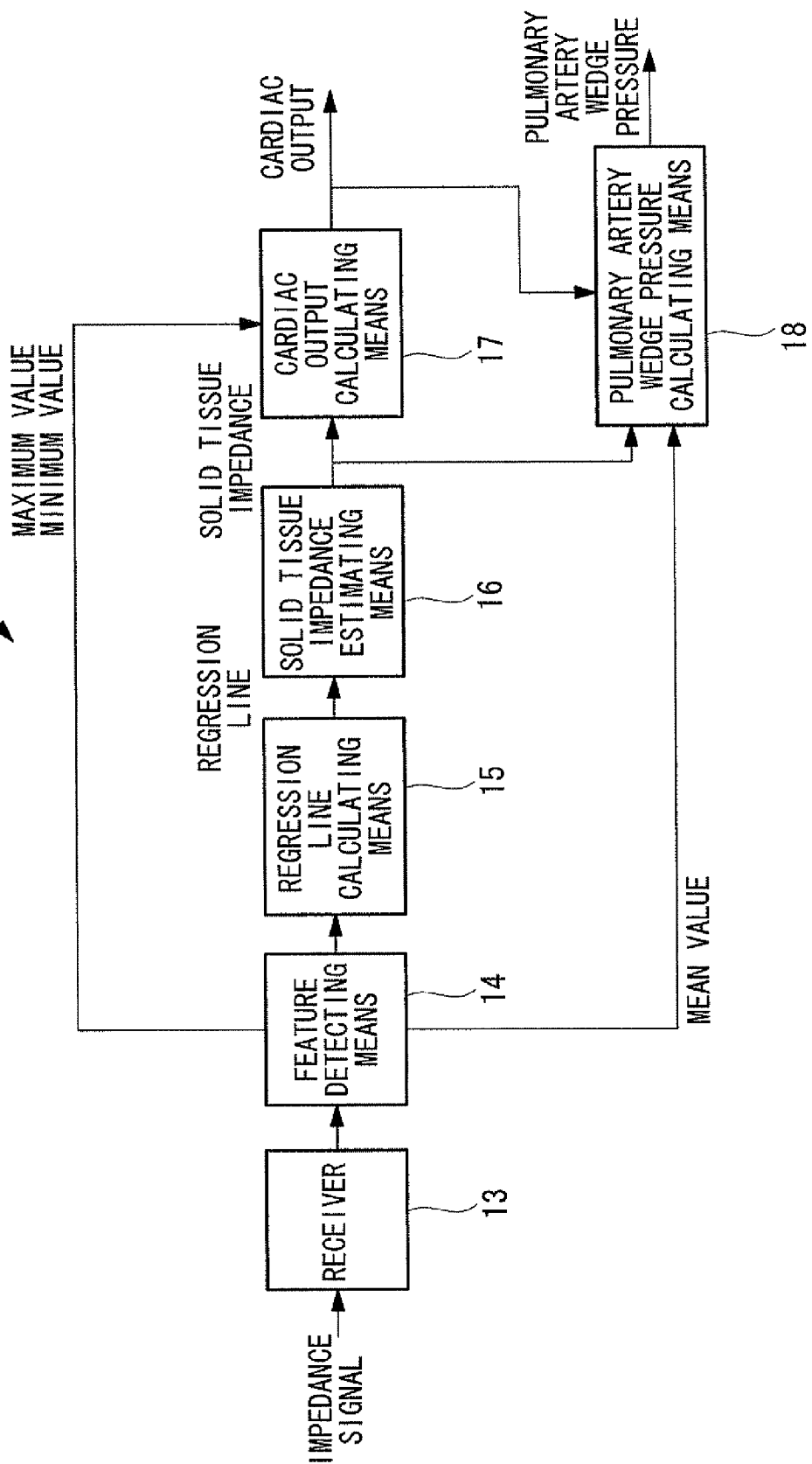
FIG. 3 is a block diagram showing the cardiac output and pulmonary artery wedge pressure monitoring device which is a part of the cardiac output and pulmonary artery wedge pressure monitoring system shown in FIG. 1.

As shown in FIG. 3, the cardiac output and pulmonary artery wedge pressure monitoring device 3 includes a receiver 13 for receiving the impedance signal between the second electrode 7 and the can electrode 5 which is detected by the implantable defibrillator 2; a feature detecting means 14 for extracting the maximum, minimum and mean values of the received impedance signal in each beat; a regression line calculating means 15 for calculating the regression line S between the maximum value and the minimum value of each data set extracted from impedance signal; a solid tissue impedance estimating means 16 for estimating the solid tissue impedance Zs by obtaining the impedance at the intersection between the regression line S calculated by regression line calculating means 15 and the line of identity; a cardiac output calculating means 17 for calculating the cardiac output using the solid tissue impedance Zs estimated by the solid tissue impedance estimating means 16; and a pulmonary artery wedge pressure calculating means 18 for calculating the pulmonary artery wedge pressure using the solid tissue impedance Zs estimated by the solid tissue impedance estimating means 16 and the cardiac output calculated by the cardiac output calculating means 17.

The method for calculating cardiac output using the cardiac output and pulmonary artery wedge pressure monitoring system 1 according to this embodiment will be explained.

When an alternating current is injected between the can electrode 5 and the first electrode 6 by the implantable defibrillator 2, the effective conductive volume in the left lung between the electrodes 5, 6 remains constant. As indicated by the formula below, the impedance signal Z measured between the can electrode 5 and the second electrode 7 is the sum of blood impedance Zp which arises from the pulmonary circulatory blood volume in the effective conductive volume, and the solid tissue impedance Zs that arises from components other than blood such as the pleura, pericardium, musculature, etc. in the effective conductive volume.

$$Z = Zp + Zs$$

Blood impedance Zp varies according to changes in blood volume, while solid tissue impedance Zs remains constant. Since pulmonary circulatory blood volume as a whole or within the effective conductive volume decreases during diastole, the blood impedance Zp increases. Specifically, the blood impedance Zp as well as the total impedance Z reaches maximal (Zmax) where the blood volume in the effective conductive volume becomes minimal.

On the other hand, since the pulmonary circulatory blood volume as a whole or within the effective conductive volume increases during systole, the blood impedance Zp decreases. Specifically, the blood impedance Zp as well as the total impedance Z reaches minimal (Zmin) at the point where the blood volume in the effective conductive volume becomes maximal.

Using the maximum impedance signal Zmax and the minimum impedance signal Zmin extracted above, cardiac output CO can be obtained by the following formula (1):

$$CO = k \times (1/(Zmin - Zs) - 1/(Zmax - Zs)) \times HR \qquad (1)$$

where HR is the heart rate and can be obtained by, for example, detecting the number of times that a maximum or minimum impedance appears over one minute. k is a correction factor and can be determined by measuring actual cardiac output using, for example, the Swan-Ganz catheter, echocardiography, etc.

Figure 4:
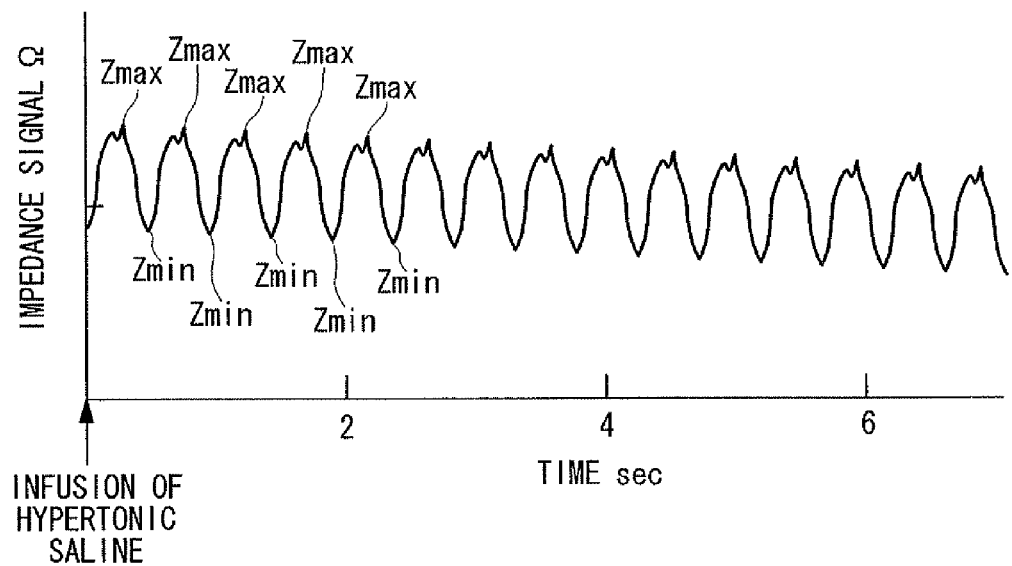
FIG. 4 is a graph showing the changes in the impedance signal during a specific period of time following infusion of hypertonic saline into the pulmonary circulation, which is described in the method for estimating solid tissue impedance according to an embodiment of the present invention.

Before calculating the cardiac output, one has to determine Zs by the following procedures. A bolus of hypertonic saline is first infused into the pulmonary circulation. As a result, as shown in FIG. 4, the impedance signal Z between the second electrode 7 and the can electrode 5 begins to decline at the arrival of the hypertonic saline at the pulmonary circulation. The impedance signals Z over multiple cycles are obtained.

Cardiac output and pulmonary artery wedge pressure monitoring device 3 receives the impedance signal Z over multiple cycles, and the maximum impedance signal Zmax and the minimum impedance signal Zmin within each cycle are extracted by the feature detecting means 14.

Figure 5:
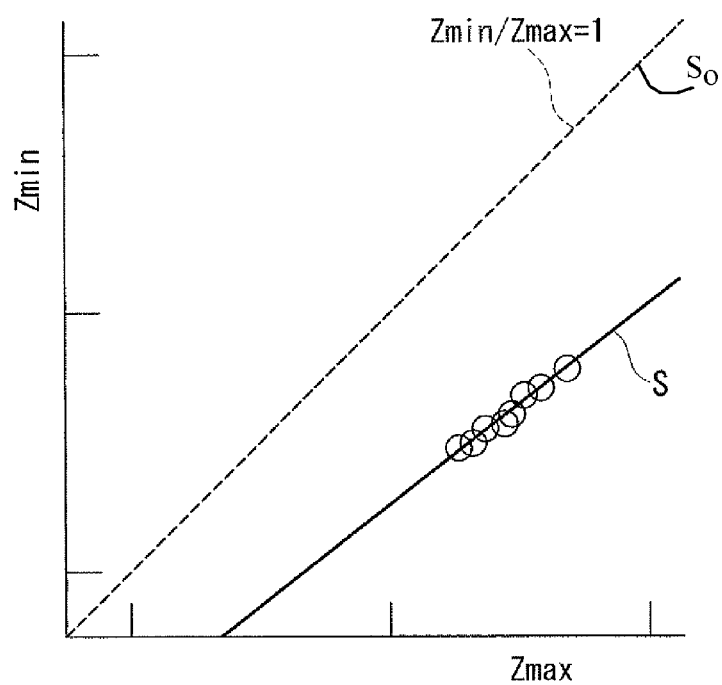
FIG. 5 is a graph showing the correlation between the maximum value and the minimum value of the impedance signal shown in FIG. 4.

Regression line calculating means 15 calculates a regression line by, for example, plotting the minimum impedance signal Zmin (for the vertical axis) against the maximum impedance signal Zmin (for the horizontal axis) of each of multiple data sets of impedance signal Z, as shown in FIG. 5. The dashed line in FIG. 5 is the line of identity.

At the intersection P between the regression line S and the line of identity $S_0$, the blood impedance becomes effectively zero. Since the blood impedance Zp becomes zero, the impedance at the intersection Z is equal to Zs.

Figure 6:
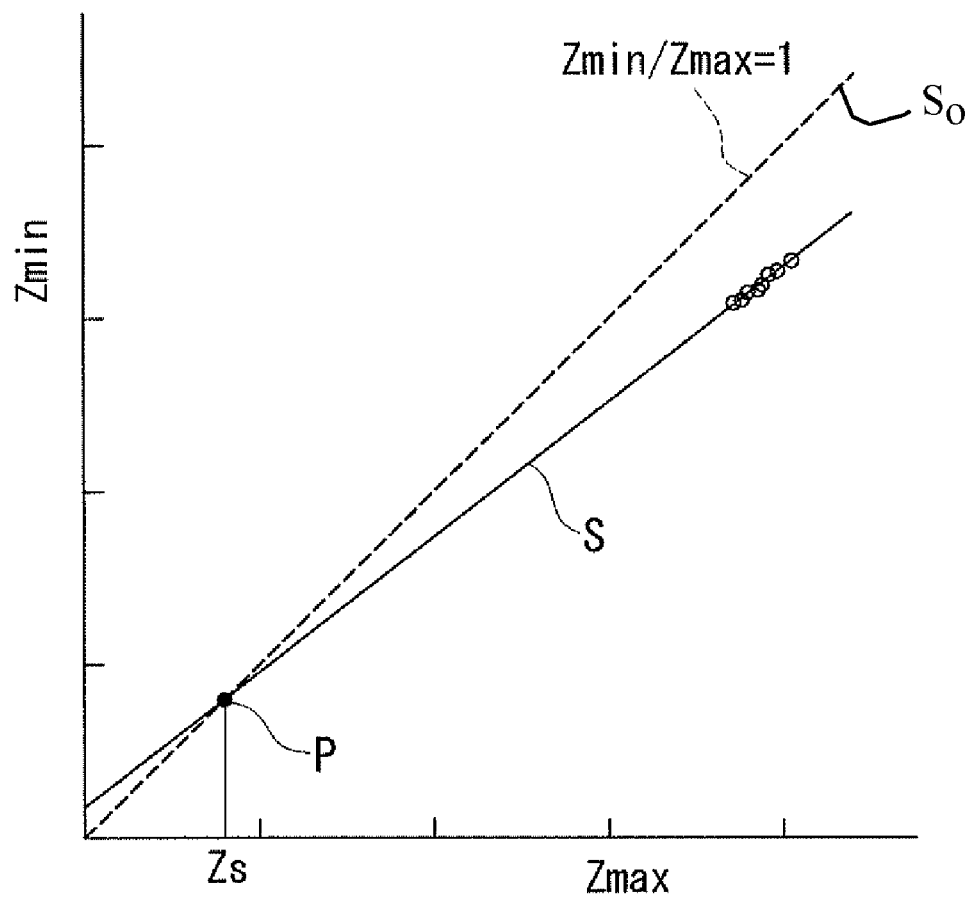
FIG. 6 is a graph explaining the method of estimating the solid tissue impedance from the intersection between the line of identity and the regression line between the maximum value and the minimum value of the impedance signal shown in FIG. 5.
Figure 7:
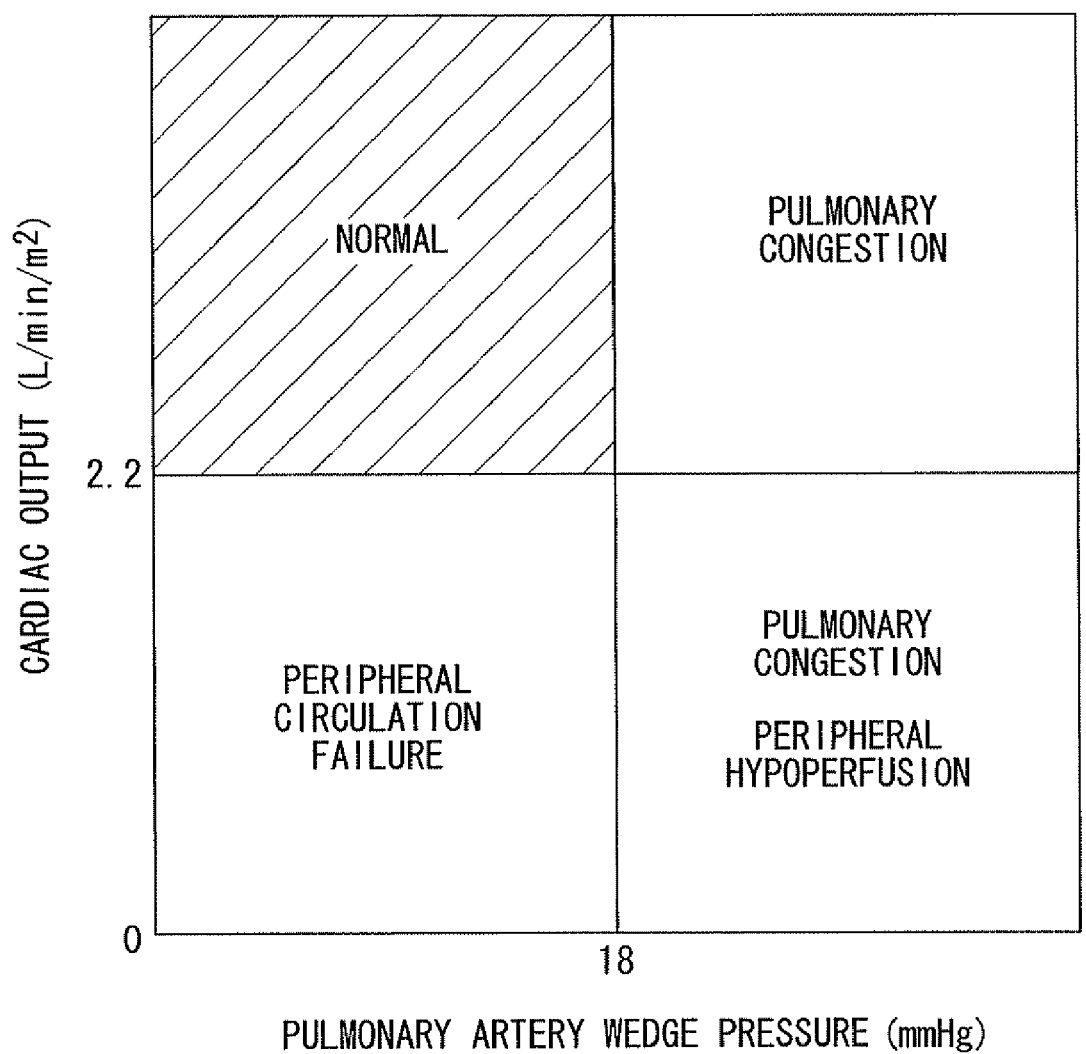
FIG. 7 is a diagram showing the Forrester's classification by cardiac output and pulmonary artery wedge pressure.

As shown in FIG. 6, the solid tissue impedance estimating means 16 extrapolates the regression line S, obtained by plotting the minimum impedance Zmin against the maximum impedance Zmax of each of multiple data sets during the specific period following the infusion of the hypertonic saline into the pulmonary circulation, and the intersection between the regression line S and the line of identity $S_0$ is obtained. As a result, one can accurately estimate the solid tissue impedance Zs.

Once the solid tissue impedance signal Zs has been estimated, the cardiac output calculating means 17 calculates cardiac output using the maximum impedance Zmax and the minimum impedance Zmin of the unperturbed cycles extracted by the feature detecting means 14. As a result, one can accurately calculate cardiac output by the formula (1) and monitor cardiac output continuously.

As explained above, the solid tissue impedance Zs can be accurately estimated using the cardiac output and pulmonary artery wedge pressure monitoring system 1 according to the embodiment. As a result, cardiac output can be accurately calculated and continuously monitored. In particular, the implanted defibrillator 2 eliminates the use of body surface electrodes preventing from the problem of electrode instability and inconvenient measurements. In addition, since the electrodes 6, 7 are inserted into the coronary vein, one can avoid high-risk problems such as thrombosis or infection, which would occur with electrodes in the left ventricle.

In the present embodiment, a can electrode is used as a single electrode, namely simultaneously for injecting current and for voltage measurements. However, the can electrode may be separated into two parts insulated with each other so that one injects current and the other measures voltage. This enables one to measure voltage with two electrodes independent of current injection.

The method for calculating the pulmonary artery wedge pressure using the cardiac output and pulmonary artery wedge pressure monitoring system 1 according to this embodiment will be explained. The total pulmonary circulatory blood volume V, pulmonary artery wedge pressure PAWP, and cardiac output CO are related according to the following formula (2):

$$PAWP = V \times A - CO \times B \quad (2)$$

where A and B are constants that are known as universal even between different individuals.

As described above, one can calculate the blood impedance Zp arising from the blood in the effective conductive volume formed between the can electrode 5 and the second electrode 7. If the pulmonary circulatory blood volume Vp in the effective conductive volume is proportional to the total pulmonary circulatory blood volume V, $$V = \alpha \times Vp \quad (3)$$

where $\alpha$ is the proportionality constant.

The pulmonary circulatory blood volume Vp in the effective conductive volume is inversely proportional to the blood impedance Zp. Accordingly, modifying formula (3) yields:

$$V = \alpha \times \beta / Zp = C / Zp \quad (4)$$

where $\beta$ is a proportionality constant and $C = \alpha \times \beta$.
Substituting formula (4) into formula (2) yields:

$$PAWP = A \times C / Zp - CO \times B \quad (5)$$

where Zp is the time-averaged blood impedance.
Thus, formula (5) becomes:

$$PAWP = A \times C / (Zmean - Zs) - CO \times B \quad (B)$$

where Zmean is the mean impedance signal.

Once the solid tissue impedance signal Zs has been estimated, the pulmonary artery wedge pressure calculating means 18 calculates the pulmonary artery wedge pressure using the mean impedance signal Zmean of the unperturbed cycles extracted by the feature detecting means 14. As a result, one can accurately calculate the pulmonary artery wedge pressure by the formula (B) and monitor pulmonary artery wedge pressure continuously. Upon implantation of the defibrillator 2 into the patient, the correction factor C can be determined from actual measurements of cardiac output and pulmonary artery wedge pressure using for example, the Swan-Ganz catheter, echocardiography, etc.

It has been the conventional practice to assume that the pulmonary artery wedge pressure PAWP is inversely proportional to the impedance signal Z, and to estimate the pulmonary artery wedge pressure PAWP from the reciprocal of the impedance signal Z. As heart failure progresses and cardiac function deteriorates, a decrease in cardiac output CO usually accompanies an increase in the total pulmonary blood volume V. Accordingly, an increase in pulmonary artery wedge pressure PAWP can be properly conjectured qualitatively.

However, the quantitative estimate of pulmonary artery wedge pressure PAWP can be inaccurate due to changes in cardiac output CO. Even when the cardiac function of a patient is actually deteriorating, pulmonary artery wedge pressure PAWP is rising and pulmonary edema is progressing, changes in pulmonary blood volume alone may not be large enough to detect these changes. Conversely, conventional methods using pulmonary blood volume alone may also overdiagnose the cardiac deterioration even when cardiac function has improved, leading to the administration of unnecessary treatment to the patient.

According to this embodiment, the present invention is advantageous in calculating pulmonary artery wedge pressure PAWP based on not only the pulmonary blood impedance signal Zp but also cardiac output CO, and preventing problems described above by accurately estimating the pulmonary artery wedge pressure PAWP.

The cardiac output and pulmonary artery wedge pressure monitoring device 3 can be combined with a conventionally developed defibrillator 2.

Furthermore, by monitoring the changes in cardiac function of patients using accurate cardiac output and pulmonary artery wedge pressure values, one can adjust individual therapy according to the Forrester's functional classification (FIG. 7) of each patient, and detect deterioration earlier and initiate therapy sooner. As a result, the present invention has the advantage of improving patient prognosis and quality of life (QOL) indicators such as duration of hospital stay, etc.

What is claimed is:

1. A solid tissue impedance estimating method for estimating a solid tissue impedance arising from a solid tissue, the method comprising:
    infusing a hypertonic saline solution into pulmonary circulation of a patient;
    measuring a minimum impedance value and a maximum impedance value for each of a predetermined number of cardiac cycles, after the hypertonic saline solution is infused, wherein the measured minimum impedance values and measured maximum impedance values form data sets, wherein each of the data sets contains the measured maximum impedance value and the measured minimum impedance value of the impedance signal during each of the cardiac cycles, and wherein the minimum and maximum impedance signals are obtained between a can electrode implanted in a left thoracic wall and an electrode inserted into a coronary vein;
    plotting the measured maximum impedance values and the measured minimum impedance values against each other and performing a linear regression to create a linear regression line;
    determining an impedance at an intersection between a line of identity and the linear regression line, wherein the impedance is a solid tissue impedance, and wherein the line of identity is a line where the minimum impedance values divided by the maximum impedance values is 1; and
    outputting the solid tissue impedance value based on the intersection between the line of identity and the linear regression line.

2. A cardiac output calculating method, the method comprising:
    estimating a solid tissue impedance value based on the method of claim 1;
    measuring a heart rate;
    measuring a maximum impedance value and a minimum impedance value of one additional cardiac cycle; and
    calculating the cardiac output based on formula (I), wherein formula (I) is $$CO = k \times (1/(Zmin - Zs) - 1/(Zmax - Zs)) \times HR$$

wherein CO is cardiac output, k is a correction factor, Zmin is the minimum impedance value of the one additional cardiac cycle, Zmax is the maximum impedance value of the one additional cardiac cycle, Zs is the estimated solid tissue impedance and HR is the heart rate.

3. A pulmonary artery wedge pressure calculating method comprising:
    estimating a solid tissue impedance value based on the method according to claim 1;
    measuring a heart rate;
    measuring a maximum impedance value and a minimum impedance value during one additional cardiac cycle;
    calculating a mean impedance value during the one additional cardiac cycle;
    calculating a cardiac output according to formula (1); and
    calculating a pulmonary artery wedge pressure according to formula (2):

$$CO = k \times (1/(Zmin - Zs) - 1/(Zmax - Zs)) \times HR \quad (1)$$

$$PAWP = A \times C/(Zmean - Zs) - CO \times B \quad (2)$$

wherein CO is cardiac output, k is a correction factor, Zmin is the minimum impedance value of the one additional cardiac cycle, Zmax is the maximum impedance value of the one additional cardiac cycle, HR is the heart rate, PAWP is pulmonary artery wedge pressure, A, B, C are correction factors, Zmean is the mean impedance value during the one additional cardiac cycle, and Zs is the estimated solid tissue impedance value.

* * * * *